United States Patent [19]
Casey

[11] Patent Number: 4,822,348
[45] Date of Patent: Apr. 18, 1989

[54] SURGICAL CLIPS

[76] Inventor: Donn Casey, 141 Newmarket Rd., Cambridge, England, CB5 8HA

[21] Appl. No.: 49,613

[22] Filed: May 13, 1987

[51] Int. Cl.⁴ ............................................. A61B 17/12
[52] U.S. Cl. ................................ 604/346; 128/132.5
[58] Field of Search ............... 128/346, 325, 326, 1 R; 24/460–462

[56] References Cited

U.S. PATENT DOCUMENTS

| | | |
|---|---|---|
| 3,766,925 | 10/1977 | Rubricius . |
| 3,807,906 | 4/1974 | Rafferty et al. ................. 128/346 X |
| 3,882,854 | 5/1975 | Hulka et al. . |
| 3,926,145 | 12/1975 | Bleier et al. . |
| 4,020,530 | 5/1977 | Sartore . |
| 4,112,951 | 9/1978 | Hulka et al. . |
| 4,188,953 | 2/1980 | Klieman et al. . |
| 4,212,303 | 7/1980 | Nolan . |
| 4,337,774 | 7/1982 | Perlin . |
| 4,346,869 | 8/1982 | MacNeill ............................. 128/346 |
| 4,394,864 | 7/1983 | Sandhaus . |
| 4,487,205 | 12/1984 | Giovanni et al. .................... 128/326 |
| 4,489,725 | 12/1984 | Casey et al. .......................... 128/346 |

FOREIGN PATENT DOCUMENTS

| | | |
|---|---|---|
| 0069653 | 1/1983 | European Pat. Off. . |
| 0095249 | 11/1983 | European Pat. Off. . |
| 0105797 | 4/1984 | European Pat. Off. . |
| 0122046 | 10/1984 | European Pat. Off. . |
| 0310321 | 5/1934 | United Kingdom . |
| 0651186 | 5/1951 | United Kingdom . |
| 0668771 | 3/1952 | United Kingdom . |
| 0941562 | 11/1963 | United Kingdom . |
| 1020035 | 2/1966 | United Kingdom . |
| 1021280 | 3/1966 | United Kingdom . |
| 1124914 | 8/1968 | United Kingdom . |
| 1141389 | 1/1969 | United Kingdom . |
| 1253789 | 11/1971 | United Kingdom . |
| 1392216 | 4/1975 | United Kingdom . |
| 1530282 | 10/1978 | United Kingdom . |
| 2043157 | 10/1980 | United Kingdom . |
| 2055953 | 3/1981 | United Kingdom . |
| 2069848 | 9/1981 | United Kingdom . |
| 2097851 | 11/1982 | United Kingdom . |
| 8303345 | 10/1988 | World Int. Prop. O. . |

*Primary Examiner*—Stephen C. Pellegrino
*Attorney, Agent, or Firm*—Robert F. O'Connell

[57] ABSTRACT

A surgical clip of plastics material for performing sexual sterilization comprises two jaws hinged to move from an open position to the closed position shown, in which a Fallopian tube is occluded. A catch mechanism engages when the jaws reach their closed position, and locks the jaws closed. The location of the catch mechanism in the vicinity of the hinge ensures that it does not contact the vulnerable mesosalpinx, thus reducing the risk of bleeding. Interdigitated teeth and a curved, springy tongue prevent the tube escaping from the clip as the jaws close. The teeth are rounded and are loosely interdigitated to reduce the risk of damage to the mesosalpinx. A resilient lining on the jaw biasses them apart. The clip will spring back open during application if it has not been closed sufficiently to engage the catch mechanism. The biasing also enables the clip to be located firmly in an applicator before closure.

18 Claims, 3 Drawing Sheets

4,822,348

SURGICAL CLIPS

BACKGROUND OF THE INVENTION

The present invention relates to surgical clips for occluding bodily ducts, and, in particular to clips for performing sexual sterilization.

It is known to sterilize females by surgically applying clips to the Fallopian tubes. The clips have two jaws which are closed on a tube, thereby occluding the tube to prevent gametes passing. An individual is rendered sterile by clipping both tubes. The use of clips allows the process to be reversed in many cases, if required, by cutting out the devitalised length of tube and rejoining the remaining vital portions. Clips are known which devitalise a length of tube of only a few millimeters.

A design of clip must satisfy various medical requirements if it is to be successful. The following are among the most important of these requirements.

Firstly, the clip must overcome the tendency of the Fallopian tube to escape from the clip during the application process.

A second requirement is that application of the clip be atraumatic, that is rupture of blood vessels in the mesosalpinx is avoided. The mesosalpinx is a sheet of tissue containing blood vessels for supplying the Fallopian tube, which runs along one edge of the sheet. Rupturing of the mesosalpinx blood vessels, causing bleeding, could occur either as a result of a flaw in the design of the clip, or as a result of insufficiently careful application.

Finally, the clip must meet the normal medical requirements of non-toxicity and should also be effective against recanalization (re-opening) of the Fallopian tube after the clip has been applied.

A principle cause of recanalization is necrosis of the muscular tissue surrounding the lumen of the Fallopian tube. As necrosis occurs, the thickness of this tissue may decrease, so allowing the lumen to expand and reopen, and allowing gametes to pass once more along the lumen. Recanalization caused by the clip falling off after application must also be prevented.

Various clips have been proposed which incorporate catch mechanisms for holding the clips in place after application, or means for holding the tube between the jaws during application. These involve some traumatic danger of rupturing and bleeding. In some, relatively sharp edges come into contact with the mesosalpinx. In another, a spike engages the tube as the jaws close, and there is a significant risk of blood vessels being punctured.

There exists a need for a surgical clip which can be used relatively easily, quickly and safely to perform sexual sterilizations with reduced risk of bleeding, and which will remain securely in position after application. Moreover, there is a need for a clip which is amenable to relatively cheap mass production for supply to, for instance, the so-called Third World.

SUMMARY OF THE INVENTION

In a first aspect, the invention provides a surgical clip for performing sexual sterilization, comprising two rigid jaws hinged together to form a mouth for receiving a bodily duct to be occluded by closing the jaws. The clip comprises one or more teeth at the free end of the jaws, the teeth and the jaws being so arranged and dimensioned that the teeth on the respective jaws mesh with one another to prevent the duct moving out from between the jaws longitudinally thereof when the jaws are fully closed.

In a second aspect, the invention provides a surgical clip comprising a trapping member resiliently biassed away from one jaw and towards the other jaw, to restrict the opening of the mouth, whereby the trapping member and the other jaw trap a duct within the mouth in the moment before the jaws are fully closed.

Preferably, the catch mechanism is located in the vicinity of the hinge.

The location of the catch mechanism in the vicinity of the hinge ensures that there is no danger of the elements of the catch mechanism engaging the mesosalpinx and causing trauma. The regions of the jaws remote from the catch mechanism which do engage tissue can be designed primarily with a view to avoiding bleeding.

Preferred features of each aspect of the invention are defined in the subsidiary claims set out below.

BRIEF DESCRIPTION OF THE DRAWINGS

One embodiment of a clip according to the present invention will now be described in detail by way of example and with reference to the accompanying drawings in which.

DETAILED DESCRIPTION OF A PREFERRED EMBODIMENT

Figure 1:
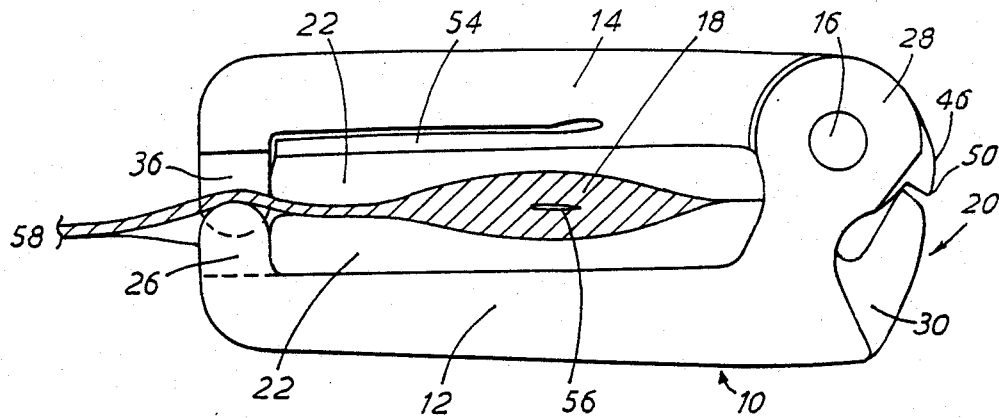
FIG. 1 shows a clip according to the invention, closed around a Fallopian tube.

FIG. 1 shows a surgical clip 10 for performing sexual sterilization. The clip comprises two jaws 12,14 connected by a hinge 16 and movable between an open position (FIG. 5) in which a Fallopian tube 18 may be introduced between the jaws, and a closed position (FIG. 1) in which a tube so introduced is occluded by the jaws. Each jaw has moulded on it a resilient lining 22. The clip 10 further comprises a catch mechanism 20 located in the vicinity of the hinge 16 and which engages, upon the jaws 12,14 reaching their closed position, to lock the jaws in that position.

Figure 2:
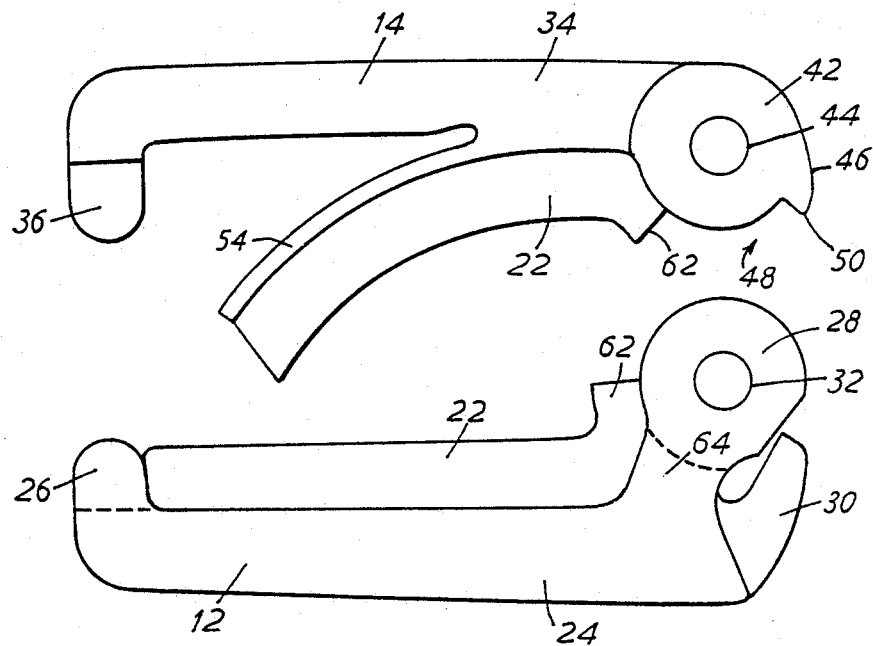
FIG. 2 shows the jaws of the clip of FIG. 1, disassembled.

The jaws are shown separated in FIG. 2. The bottom jaw 12 comprises a rigid shank 24. Two teeth 26 (see also FIG. 3) are formed at one end of the shank 24 and integrally therewith. The teeth 26 project in a direction generally perpendicular to the shank 24, towards the top jaw 14 in the assembled clip. The teeth 26 have smooth surfaces and rounded edges, to reduce the risk of damage to tissue.

At the other end of the shank are formed two spaced, generally disc-like extensions 28 of the jaw 12, and a straight resilient finger 30. The centres of the discs 28 are aligned, and holes 32 are provided at the centre of the discs for receiving a pivot pin 52 to form the hinge between the jaws. The finger 30 forms part of the catch mechanism to be described.

The top jaw 14 also comprises a rigid shank 34. A single tooth 36 is integrally formed at one end of the shank 34, projecting in a direction generally perpendicular to the shank 34. The tooth 36 has a smooth surface and rounded edges. In the assembled clip, the tooth 36 projects towards the first jaw 12. In the closed position of the clip, FIG. 3, the tooth 36 lies between, or is "interdigitated" with the teeth 26. The dimensions of the teeth 26,36 are chosen so that a channel of finite width 38 exists between the interdigitated teeth. The channel 38 allows the mesosalpinx to be located between the teeth 26,36, in the channel 38, with a low risk of its being punctured or ruptured.

At the other end of the jaw 14, a single, generally disc-like extension 42 is provided, integral with the shank 34. The disc is provided with a hole 44 for receiving the pivot pin 52 of the hinge 16.

The edge, or circumferential surface 46 of the disc 42 forms part of the catch mechanism 20. The surface 46 has a discontinuity 48 in the form of a step with a lip 50. The step surface 48 runs generally radially with respect to the axis of the hole 44, from the lip 50. The radius of the surface 46 from the hole 44 gradually decreases away from the lip 50 in an anti-clockwise direction as seen in FIG. 2.

Figure 4:
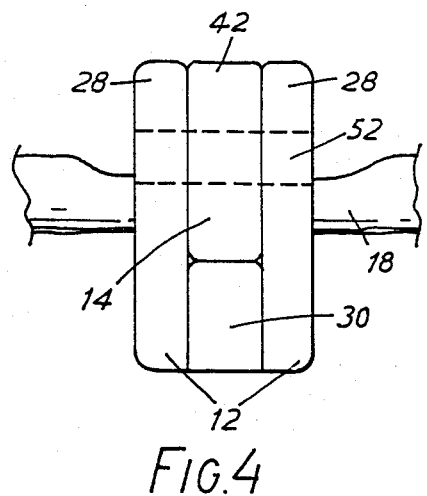

In the assembled clip 10, the disc 42 lies between the discs 28 (FIG. 4). A pivot pin 52 is located in the holes 32, 44 and allows the disc 42 to rotate relative to the discs 28 about the axis of the holes 32,44, but prevents other relative movement. A rounded stop 64 is formed on the jaw 12 between discs 28 (See FIG. 2). The stop 64 engages the lip 50 on the jaw 14 to restrict the movement of the jaws 14 and thus to determine the maximum degree of opening of jaw 14 with respect to jaw 12. The finger 30 rides over the surface 46 in a relationship determined by the angle between the jaws 12,14.

The jaw 14 has a resilient springy tongue 54. The tongue 54 is a relatively long, thin strip of resilient material which is integral at one end with the shank 34, and also has a free portion. The free portion is pre-formed to curve away from the shank 34, so that when the clip is open (FIG. 5), the end of the tongue 54 nearest the mouth 40 is spaced significantly from the jaw 14 in a direction towards the jaw 12. Accordingly, the resilient lining carried by the tongue 54 partially restricts the opening 40 even when the clip is open.

Figure 6:
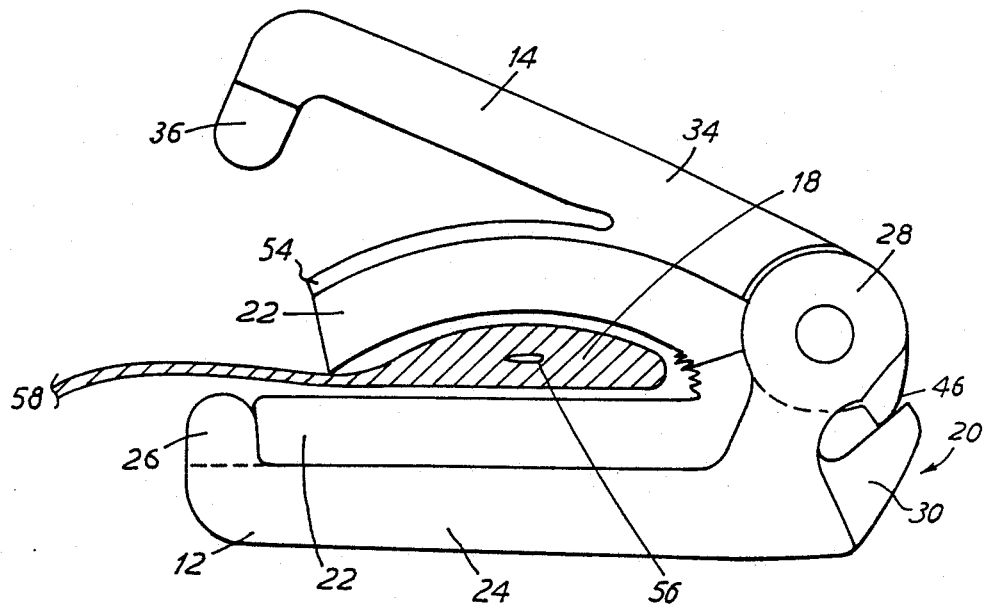
FIG. 6 shows the clip partly closed.
Figure 5:
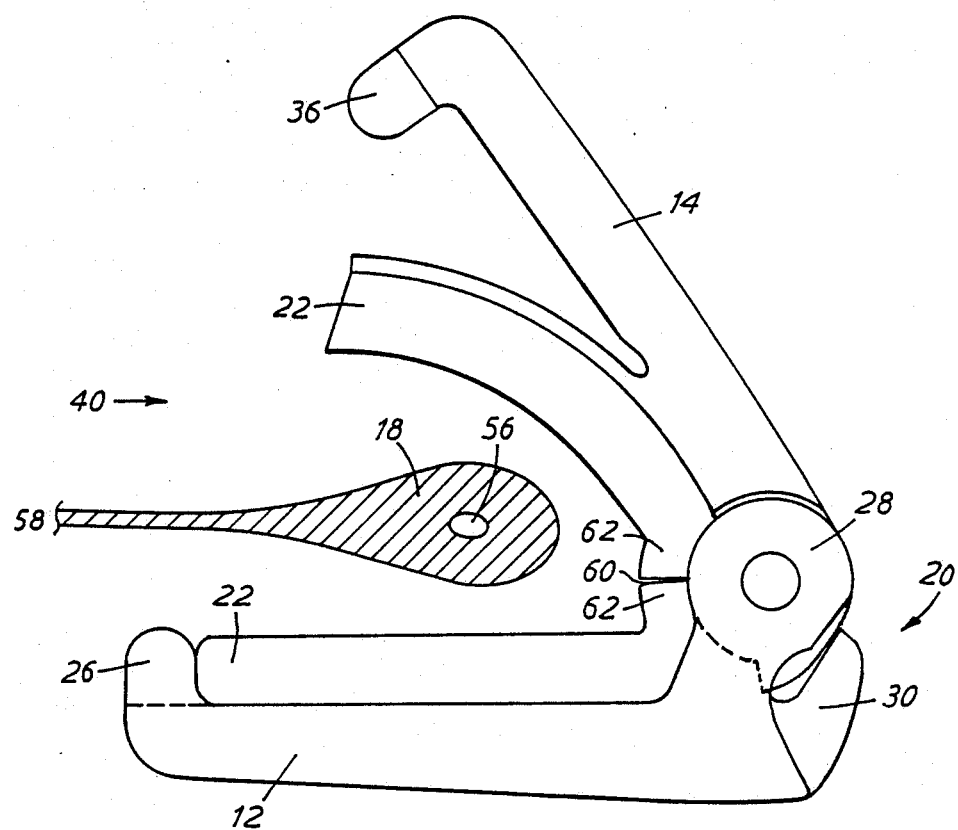
FIG. 5 shows the clip in its fully open position.

The application of a clip 10 to perform a partial sexual sterilization by occluding a single Fallopian tube 18 will now be described, with particular reference to FIGS. 1, 5 and 6.

With the clip 10 initially in its fully open position (FIG. 5) the Fallopian tube 18, including the lumen 56 and mesosalpinx 58 are placed in the mouth 40 formed between the jaws 12, 14.

The tube 18 then occupies a plane generally perpendicular to the plane of the jaws 12,14. The tube 18 is free to move in and out of the mouth 40, although the tongue 54 and teeth 26,36 partially restrict the mouth 40. The finger 30 is outside but is spaced from the surface 46.

In use, the jaws 12,14 hinge together to close the mouth 40. Eventually an intermediate position (FIG. 6) is reached. In this position the lining 22 carried on the tongue 54 has approached and just reached the lining 22 carried on the jaw 12 and the lining is beginning to apply light pressure to the mesosalpinx 58. However, substantially no risk of tearing exists, because of the resilient nature of the lining. Further into the mouth, the lining is beginning to squeeze the tissue around the lumen 56. As this pressure increases, there will be a tendency for the Fallopian tube to move away from the hinge of the clip, towards the mouth, and unless checked, it could eventually escape from the clip. The restriction of the mouth by the tongue 54 and lining 22 provides a gentle check on this movement and so overcomes this tendency.

Figure 3:
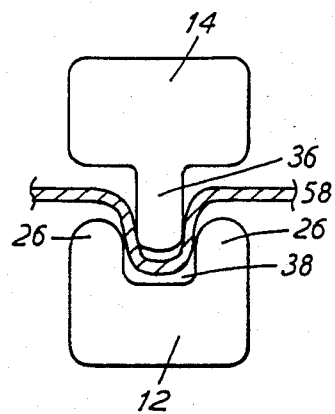
FIGS. 3 and 4 are views of the clip of FIG. 1 in its closed position and viewed from the left and right respectively, as seen in FIG. 1.

A second and final check on the movement is provided by the teeth 26,36 as the jaws 12 and 14 move further towards one another, that is, towards the position shown in FIGS. 1 and 3. The jaws 12,14, the teeth 26,36, and the hinge provide a loop which surrounds the Fallopian tube and retains it in the mouth.

As the jaws 12,14 approach this position, the mesosalpinx will begin to deform in the region of the teeth 26,36 so as to occupy the channel 38 which forms between the teeth as they interdigitate. The width of the channel 38 and the rounded smoothness of the teeth ensures that there is little risk of the teeth rupturing the blood vessels of the mesosalpinx as the jaws close.

During the approach to the final position, the surface 46 has rotated relative to the finger 30. The changing radius of the surface 46 provides a cam profile which causes the finger 30 to be deformed as the rotation progresses. This causes a bias to exist between the surfaces, by virtue of the resilience of the finger. The maximum deformation and bias occurs just before the jaws reach their final position, when the finger 30 is at its outermost position, forced out by the lip 50.

The biassing between the surfaces, which increases as the jaws close, tends to urge the jaws back to their open position. This reverse movement is also urged by the lining 22. A region 60 of the lining (FIG. 5) extends to form two projecting studs 62, near the hinge, is compressed by the jaws as they close, and biasses them to their open position. Thus, if the pressure closing the jaws 12,14 is released before the catch mechanism has engaged, the jaws will spring open, alerting the surgeon that the clip has not yet closed.

Any further closing movement causes the finger to move past the lip 50. Contact between the surface 46 and the finger 30 then ceases and the finger 30 relaxes to its natural shape, simultaneously dropping down the step discontinuity 48. This causes some further closing movement to the fully closed position shown in FIG. 1. In this position, the lumen 56 is fully occluded. The lining 22 is under compression, to compensate for subsequent muscular necrosis. The resilient tongue 54 folds back almost completely against the rigid shank 34 and its trapping function is then taken over largely by the interdigitating teeth 26,36. The mesosalpinx is folded to occupy the channel 38 (see FIG. 3). The catch mechanism 20 is engaged to lock the jaws in the fully closed position. The locking arises because the finger 30 cannot rise up to the lip 50, to run on the surface 46, unless the finger is deformed against its resilience. No means exist to provide this deformation unless the catch is deliberately interferred with. Accordingly, if the jaws 12, 14 remain closed when the closing force on them is released, the surgeon can be confident that the clip has been fully closed.

In the fully closed position, the interdigitated teeth prevent the tube escaping from the mouth.

The catch mechanism 20 serves to retain the jaws in the fully closed position against the outward biasing provided by the resilient linings 22 which is under compression. Thus, it will be appreciated that the jaws of the clip, once it is in place, do not exert any compressive force on the duct (other than the relatively gentle force exerted by the resilient linings 22). This arrangement permits the teeth 26 and 36 to interdigitate loosely transversely of the pivot pin 16 so that the mesosalpinx can pass easily between them without trauma.

The clip described is intended to be manufactured from mouldable materials which lend themselves to mass production methods. For instance, the jaws and tongue may be made from a polycarbonate plastics material. Jaws made from plastics materials can relatively easily be moulded to have smooth surfaces and rounded edges, and so be substantially atraumatic in use.

The lining 22 may be moulded onto each of the jaws after they have themselves been formed by moulding. Alternatively, the lining may be moulded separately and subsequently attached to the jaws. The lining may be silicone rubber, in which case it may be moulded under the influences of heat and pressure.

Polycarbonate materials and silicone rubber have both been used in known surgical clips without known toxicity problems. The pivot pin 52 may be 'commercially pure' titanium, for instance. Titanium has the additional advantage that it is of low toxicity. Alternatively, the pin 52 may be of "Lexan" which is also of low toxicity.

The clip may be used in male or female sterilization. For female sterilization, jaws about 15 mm long, about 3 mm wide and about 7 mm high, when closed, could be used. For male sterilization, substantially smaller clips could be used to occlude the vas deferens.

The clip described can be applied by means of a simple applicator which enables a closing force to be applied remotely to a clip mounted in the applicator. Only a small closing force is required. It is envisaged that the clip would be mounted in the applicator so that the jaw 12 rests on a fixed surface, and the closing force is applied by a movable member to the jaw 14. If the closing force is removed before the clip is fully closed, the jaws will reopen, because of the dual biassing described above. Furthermore, the biassing can be used to retain the clip in the applicator until it has been closed. With a simple applicator the Fallopian tube (or vas deferens) can normally be drawn out of an incision and the clip applied externally. If a laparoscope is used a more complex applicator will be needed.

The clip described has two mechanisms for retaining a bodily duct within the mouth of the clip. In practice it is conceivable that the use of only one would be satisfactory.

What is claim is:

1. A surgical clip for performing sexual sterilization, comprising:
   two jaws hinged together to form a mouth for receiving a bodily duct to be occluded by closing the jaws; and
   an elongated trapping member of resilient material extending from a first end relatively remote from the said mouth substantially along the length of the said one jaw to a second free end relatively closer to the said mouth, the trapping member in its unstressed condition curving away form the said one jaw towards the other jaw, the trapping member acting to restrict the mouth formed by the jaws, whereby the trapping member and the said other jaw trap a duct within the mouth before the jaws are fully closed.

2. A clip according to claim 1 in which the trapping member is formed so that, as the jaws move towards one another, it bears against the other jaw before the jaws are fully closed together.

3. A clip according to claim 1, wherein the said one jaw is lined with a layer of resilient material, the layer being sufficiently thick to be in compression when the jaws are fully closed around a duct.

4. A clip according to claim 3 and further comprising a catch which engages upon the jaws when they reach their fully closed position, to lock the jaws in that position.

5. A clip according to claim 4 in which the jaws include teeth and said bodily duct includes a mesosalpinx, the jaws, in the fully closed position, being biased away from each other, the catch acting, in use, to retain the jaws in the closed position against the said biassing; and the jaws, in the fully closed position, being spaced from one another such that the teeth exert substantially no pressure on the mesosalpinx when held between them.

6. A clip according to claim 4 in which the catch mechanism is located in the vicinity of the regions where the jaws are hinged.

7. A clip according to claim 6 in which the jaws extend away to one side of said hinged region and wherein the catch mechanism is located at the other side of said hinged region.

8. A clip according to claim 6 wherein the catch mechanism comprises two opposed surfaces carried by respective ones of said jaws and biassed against each other, and wherein a first one of the surfaces has a discontinuity at a position corresponding to the closed position, and wherein the surfaces are free to ride over each other as the jaws close, until the second surface crosses the discontinuity when the closed position is reached, and wherein the second surface is thereafter prevented by the biasing from returning across the discontinuity.

9. A clip according to claim 8, wherein the discontinuity is a depression or lip in the first surface.

10. A clip according to claim 8, wherein one of the surfaces has a cam profile so shaped as to increase the biassing between the surfaces as the jaws move towards the closed position.

11. A clip according to claim 8, wherein one of the surfaces is a surface of a finger carried by the corresponding jaw.

12. A clip according to claim 11, wherein the finger is resilient, and wherein the resilience of the finger provides all or part of the biassing between the surfaces.

13. A clip according to claim 8, wherein the biasing between the opposed surfaces tends to open the jaws, if the catch mechanism has not engaged.

14. A clip according to claim 8, wherein one of the opposed surfaces is the circumferential surface of a generally disc-like extension of the corresponding jaw.

15. A clip according to claim 8, wherein the other jaw further includes a resilient material so that the surfaces of the jaws which bear on the duct are both lined with resilient material, the resilient material carried by each jaw in the vicinity of the region where the jaws are hinged bearing on the material carried by the other jaw in the vicinity of said region as the jaws close, to bias the jaws to their open position.

16. A clip according to claim 1, wherein the trapping member comprises a resilient tongue having a free portion which extends away from the one jaw towards the other jaw.

17. A clip according to claim 16, wherein the free portion of the tongue is curved.

18. A clip according to claim 1 further comprising: one or more teeth at the ends of the jaws remote from the hinge-ends of the jaws, the teeth of the jaws being so arranged and dimensioned that the teeth on the respective jaws mesh with one another to prevent the duct moving out from between the jaws longitudinally thereof when the jaws are fully closed; the teeth, when interdigitated, being spaced from one another circumferentially and longitudinally of the hinge axis of the jaws to allow them to close on a mesosalpinx without causing rupturing of blood vessels therein.

* * * * *